United States Patent [19]

Brinton, Jr.

[11] Patent Number: 5,750,116
[45] Date of Patent: May 12, 1998

[54] HAEMOPHILUS INFLUENZAE PILUS VACCINES

[75] Inventor: Charles C. Brinton, Jr., Export, Pa.

[73] Assignee: Bactex, Inc., Pittsburgh, Pa.

[21] Appl. No.: 459,823

[22] Filed: Jun. 2, 1995

[51] Int. Cl.$^6$ .................... A61K 39/02; A61K 39/102
[52] U.S. Cl. ........................ 424/242.1; 424/256.1
[58] Field of Search ...................... 424/242.1, 256.1

[56] References Cited

U.S. PATENT DOCUMENTS 5,336,490  8/1994  Brinton, Jr. et al. ............... 424/242.1

OTHER PUBLICATIONS

Van Ham et al., 1992. J. Infect. Dis. vol. 165 (Suppl.1) pp. S97–S99.
Gilsdorf et al. 1990. Infect. Immun. vol. 58. pp. 2252–2257.

Primary Examiner—James C. Housel
Assistant Examiner—Jennifer Shaver
Attorney, Agent, or Firm—Omri M. Behr, Esq.

[57] ABSTRACT

Purified pili of serotype LKP9 through LKP16 and LKP18 through LKP20 from *Haemophilus influenzae*. There is further provided a purified multivalent intact pilus vaccine composition for protecting subjects against infections caused by piliated *H. influenzae* which comprises a pharmaceutically acceptable carrier and whole *H. influenzae* pili, designated vaccine pili, previously separated from other *H. influenzae* components, in an amount capable of raising the antibody level of the subject to a level sufficient to provide such protection, said vaccine comprising pili of at least one type selected from a group of pili types designated LKP9 through LKP16 and LKP18 through LKP20, said vaccine pili being agglutinable by antisera derived from LKP pili purified from at least one strain of *H. influenzae*. Methods of immunizing employing said vaccines are also provided.

10 Claims, 5 Drawing Sheets

CLJ11

CLJ10

CLJ12

ANTIGEN
OD AT 540nm

| STRAINS | | LKP1 88-0295 | LKP2 61-0568 | LKP3 EAGAN | LKP4 66-1249 | LKP5 81-0384 | LKP6 86-0612 | LKP7 87-0297 | LKP9 86-0214 | LKP10 86-0807 | LKP11 CB-89 | LKP12 86-0677 | LKP13 86-0762 | LKP14 86-0473 | LKP15 89-0473 | LKP16 88-0715 | LKP18 88-0909 | LKP19 88-1219 | LKP20 88-1225 |
|---|---|---|---|---|---|---|---|---|---|---|---|---|---|---|---|---|---|---|---|
| | | | | | | | | | | anti | sera | | | | | | | | |
| 86-0295 | | 12600 | | | | | | | | | | | | | | | | | |
| 61-0568 | | | 12800 | | | | | | | | | | | | | | | | |
| EAGAN | | | | 6400 | 640 | 40 | | | | | | | | | | | | | |
| 66-1249 | | 40 | | | 51200 | 60 | | | | | | | | | | | | | |
| 81-0384 | | | | 160 | | 6400 | | | | | | | | | | | | | |
| 86-0612 | | | | | | | 3200 | | | | | | | | | | | | |
| 87-0297 | | | | | | | 80 | 1600 | | | | | | | | | | | |
| 86-0214 | | | | | | | | | 6400 | | | | | | | | | | |
| 86-0807 | | | | | | | | | | 6400 | | | | | | | | | |
| CB-59 | | | | | | | | | | 80 | 25600 | 40 | | 60 | | | | | |
| 88-0677 | | | | | | | | | | | | 6400 | 40 | 20 | | | | | |
| 86-0762 | | | | | | | | | | | | | 6400 | | | | | | |
| 88-0473 | | | | | | | | | | 40 | | | | 800 | | | | | |
| 89-1163 | | | | | | | | | | | | | | | 320 | | | | |
| 88-0715 | | | | | | | | | | | | | | | | 20460 | | | 1280 |
| 88-0909 | | | | | | | | | | | | | | | | 320 | 10240 | | 1280 |
| 88-1219 | | | | | | | | | | | | | | | | | | 5120 | |
| 88-1225 | | | | | | | | | | | | | | | | 5120 | | | 1280 |

FIG. 6

HAEMOPHILUS INFLUENZAE PILUS VACCINES

BACKGROUND OF THE INVENTION

The human pathogen *Haemophilus influenzae* is responsible for a number of diseases among infants and children as well as adults. Both the encapsulated and non-encapsulated forms of the bacterium are pathogenic, with the invasive diseases (such as meningitis, epiglottitis, septic arthritis and cellulitis) caused almost exclusively by type b encapsulated strains, while mucosal diseases are mainly caused by non-type b encapsulated and non-encapsulated ($NT_b$ *H. influenzae*) strains.

Perhaps the most well known of the *H. influenzae* mucosal diseases is infant or child earache ("otitis media"). While *H. influenzae* causes only about 30% of all otitis media cases, it is the most frequent cause of recurrences of the disease, each episode of which can impair hearing. Adult *H. influenzae* diseases are principally mucosal and include chronic bronchitis, sinusitis and pneumonia. The diseases caused by *H. influenzae* can lead not only to deafness, but also to mental retardation and death.

Vaccines do exist for protection against type b encapsulated strains of *H. influenzae*. However, none of these vaccines affords any protection against mucosal *H. influenzae* diseases or prevents transmission of the infection or colonization of the human nasopharynx.

The mucosal *H. influenzae* diseases typically begin when the bacteria enter the human nasopharynx. The *H. influenzae* bacteria are generally piliated while in the nasopharynx. It is generally believed that the pili help the bacteria to bind certain cell surface receptors commonly present on the surface of cells lining the nasopharynx, thus assisting the infecting bacteria to gain a physical hold in the nasopharynx. The bacteria can then migrate to the middle ear, where they can symptoms of otitis media, particularly a painful inflammation.

There are three morphological and adhesion classes of pili on *H. influenzae* clinical isolates from different diseases and anatomical sites. The principal pilus class, termed LKP pili, has been characterized in detail. LKP pili adhere to human erythrocytes, as do many of the pili used in other vaccines. Both $NT_b$ *H. influenzae* and *H. influenzae* b strains can express LKP pili of the same serotypes, opening the possibility that one purified LKP pilus vaccine consisting of mixed serotypes can protect against several *H. influenzae* diseases.

Like other pili, the LKP type pili have as their main constituent protein pilin which forms the pilus rod. The rod is secured to the bacterium by an anchoring protein and has at its opposite end a tip adhesion protein ("adhesin").

The LKP pili are characterized by a long ("L") and thick (i.e., 4 nm in width, "K") appearance in electron micrographs; and by being positive ("P") for the ability to hemagglutinate human RBC in PBS in standard times at standard bacterial concentrations and at room temperature.

As in all natural piliated bacteria, the expression of LKP pili in *H. influenzae* is under the control of a phase variation system. In *H. influenzae*, phase variation is of two kinds: a switch on/switch off of a single pilus type and a switching among several different pilus types. Several strains of piliated *H. influenzae* which express a single LKP pilus type are subject to a reversible $P^+$ to $P^-$ and $P^-$ to $P^+$ phase transition. Both the $P^+$ and $P^-$ phases are stable during laboratory culture on chocolate agar, switching to the opposite phase only very rarely. The in vivo switching rate under more natural conditions is quite different: phase varying strains in the LKP $P^-$ phase introduced into the chinchilla middle ear switch very rapidly to the $P^+$ phase, (suggesting that the middle ear contains environmental signals favoring switching to the $P^+$ phase).

It appears that in *H. influenzae* as in *E. coli*, phase switching is a stochastic (probabilistic) process and environmental conditions affect the probabilty of different phase switches in different ways. Another way of stating this is that, even under conditions favoring switching to and better growth of one particular phase, there can and usually will be a minority of other phases in any given culture of bacteria containing a sufficient number of cells. In other words, growth conditions affect the equilibrium among phases but do not usually eliminate switching to any particular phase although the switching probability may be very low.

An important practical result of this is that, by using enrichment or selective techniques for piliated cells, one can often recover a few P+ cells from a predominantly $P^{1-}$ culture, even where the total culture may not reveal any properties characteristics of piliated bacteria and electron microscopic examination shows no or very rare piliated bacteria. A procedure called "phase cloning" has been devised for the isolation and maintenance of separate phases of a strain. In this procedure, colonies or sectors of colonies characteristic of individual phases are recognized, selected and respread on new plates. Phases may be maintained for study in this way even under environmental conditions favoring switching to another phase. (By contrast, a "phase eduction" procedure has been devised in which new phases are encouraged to appear by growing the same strain in a wide variety of different growth conditions.) Phase cloning technology may be used to maintain the different piliated phases in culture for use in vaccines.

One useful technique for enriching the number of piliated cells in a population of mainly non-piliated *H. influenzae* is hemagglutinating the bacteria with red blood cells. The piliated bacteria adhere to the red cells, agglutinate them, and form clumps; the nonpiliated ones generally do not. The red cells and adhering bacteria are separated from the non-adhering bacteria in low gravitational forces and are plated on bacterial growth media. Piliated phases are cloned and maintained by picking the resulting hemagglutination positive (HA+) colonies. LKP piliated phases can be found by this method in the majority of Hflu isolates that are not LKP piliated when cultured in the laboratory. Another useful enrichment technique is is to use aqueous polymer countercurrent distribution techniques. By means of these enrichment techniques, one can generally restrict a subculture to a particular phase, i.e., to piliated cells.

Each subculture is grown from an inoculum taken from an original sample or a previous culture and then grown or selected in a certain way which might alter its phase composition. A subculture is not a phase, but consists of a cell population which can, and usually does contain a mixture of phases. A culture will reflect the phases present in the previous culture and the eduction and selection of phases caused by the specified growth or selection conditions. One must, therefore, keep track of subcultures' line of descent from all previous cultures and the original sample. This is done by a simple numbering system in which each subculture of a prior culture is given an individual number preceded by the pedigree number of the prior culture. Replicate subcultures may not all have the same phase compositions, even when identically prepared, because of the stochastic nature of phase switching.

U.S. Pat. No. 5,336,490 (incorporated herein by reference) describes certain vaccines based on purified LKP pili. These pili were tested in the chinchilla model of otitis media in vaccine compositions against *H. influenzae* infection and disease, and found to be safe, antigenic, and to protect against both nasopharyngeal colonization and middle ear disease. Since protection is specific to the LKP pilus type administered, the vaccines preferably contain pili of more than one LKP type.

Clinical samples of *H. influenzae* pathogens have conventionally been isolated from the site of disease. Hence, the pili used in the vaccines of U.S. Pat. No. 5,336,490 are derived from *H. influenzae* isolated from the middle ear of children with otitis media.

SUMMARY

We have now identified eleven new classes of LKP pili—LKP9 through LKP 16 and LKP18 through LKP20—on *H. influenzae* by adhesion specificity, electron microscopy, and serotyping. These new LKP pilus serotypes were discovered during a bacterial epidemiology study of children in the greater Pittsburgh area who were enrolled at birth and seen regularly by otolaryngologists for 2 years. However, unlike clinical isolates collected in the past, the isolates collected during this study were from the throat and, in most cases, taken in the absence of otitis media symptoms.

Several different kinds of piliation phases were seen among these clinical isolates. Most of the isolates were in a non-LKP-piliated and non-hemagglutinating state when received. These bacteria in the isolates were enriched and selected for LKP pilus expressing phases by a two step process: first, adsorbing piliated bacteria to human red cells, settling of the agglutinated cells, and plating the bacteria/ erythrocyte aggregates on solid medium (hemadsorption); and second, testing individual colonies for hemagglutination, then selecting and replating positive colonies (phase cloning).

LKP piliation phases of the enriched cultures are identified by hemagglutination (HA) positivity, type-specific pilus antiserum agglutination, electron microscope (EM) observation of unlabeled pili, and EM observation of cultures whose pili were labeled with type-specific pilus antisera. A pilus typing scheme of 19 different, largley non-cross reacting, antisera was used (FIG. 6). The majority of cultures express a single serotype of LKP pili. A fraction of the cultures express multiple LKP types, with EM immunolabeling showing that as many as four different pilus types were expressed by some single cultures.

While phase variation studies showed that the expression of single pilus types on single or multiple LKP expressors could reversibly switch between a piliated and nonpiliated phase at relatively high rates, both piliated and nonpiliated phases were relatively stable during in vitro subculture.

Thus, Applicants have discovered that *Haemophilus influenzae* from nasopharyngeal samples provide LKP pili which when purified are useful in vaccine formulations. The first embodiment comprises purified whole LKP pili from *H. influenzae* organisms selected from the group of serotypes consisting of LKP9 through LKP 16 and LKP18 through LKP20. Suitably these whole LKP pili are derived from the group of *H. influenzae* strains consisting of: *H. influenzae* LKP9 (86-0214) ATCC Deposit No. 55771; *H. influenzae* LKP10(86-0807) ATTCC Deposit No. 55772;

*H. influenzae* LKP 11 (CB-59) ATTCC Deposit No. 55773;

*H. influenzae* LKP12 (88-0677) ATTCC Deposit No. 55774;

*H. influenzae* LKP13 (86-0762) ATTCC Deposit No. 55775;

*H. influenzae* LKP14 (88-0473) ATTCC Deposit No. 55776;

*H. influenzae* LKP15 (89-1163) ATTCC Deposit No. 55777;

*H. influenzae* LKP16 (88-0715) ATTCC Deposit No. 55778;

*H. influenzae* LKP18 (88-0909) ATTCC Deposit No. 55779;

*H. influenzae* LKP19 (88-1219) ATTCC Deposit No. 55780; and

*H. influenzae* LKP20 (88-1225) ATTCC Deposit No. 55781;

The LKP pili of *H. influenzae* may be expressed in *E. coli* by transforming a strain of *E. coli* with the appropriate fragment of *H. influenzae* genomic DNA incorporated in a vector. When one so expresses the LKP pili, one finds that a single LKP pilus type is expressed continuously, without phase variation or multiple expression. One operon which encodes the constituent proteins of the LKP1 operon of *H. influenzae* is described in U.S. patent application Ser. No. 08/277,231 filed Jul. 19, 1994, incorporated herein by reference. Other operons isolated from the genomic DNA of *H. influenzae* encode for an LKP pilus type 9 through 16 and 18 through 20. These single serotype recombinants, which may be grown in liquid medium, produce pili in large, easily purifiable quantities without other *H. influenzae* antigens. The *H. influenzae* pili expressed by these *E. coli* are easily standardized for purity, identity, concentration and potency for subsequent mixing into a multivalent vaccine, thus providing efficient pilus production.

The pilins are purified in assembled rod form by removal of the minor tip proteins and separation of rods from minors on molecular sizing columns. In their assembled form, the pilin units retain the antigenic specificity of intact pili which is conferred by the exposed surface determinants of the pilin subunits on the lateral surface of the pilus rod. Pilin rods are equally as effective multivalent vaccine components as intact pili and may have the advantage of higher purity and possibly reduced side effects.

The second embodiment comprises a purified multivalent intact pilus vaccine composition for protecting subjects against infections caused by piliated *H. influenzae* organisms which comprises a pharmaceutically acceptable carrier and whole *H. influenzae* pili, previously separated from other *H. influenzae* components, in an amount which raises the antibody level of the subject to a level sufficient to provide such protection, said vaccine comprising pili of at least one type selected from a group of pili types designated LKP9 through LKP16 through LKP18 through LKP20, said vaccine pili being agglutinable by antisera derived from pili from at least one of the following organisms LKP9 through LKP16 and LKP18 through 20. Certain suitable vaccines comprise LKP types 10, 11, 16, 18 and/or 20.

The third embodiment comprises method of protecting subjects against infections caused by piliated *H. influenzae* organisms which comprises administering to a subject in need of protection a composition which raises the antibody level of the subject to a level sufficient to provide such protection comprising: whole *H. influenzae* pili, designated vaccine pili, previously separated from other *H. influenzae* components, said composition comprising vaccine pili of at least one type selected from a group of pili types designated LKP9 through LKP16 and LKP18 through LKP20. The vaccine pili are agglutinable by antisera derived from pili from organisms of at least one strain of one of the following types:

H. influenzae LKP9 (86-0214);

H. influenzae LKP10 (86-0807);

H. influenzae LKP11 (CB-59);

H. influenzae LKP12 (88-0677);

H. influenzae LKP13 (86-0762);

H. influenzae LKP14 (88-0473);

H. influenzae LKP15 (89-1163);

H. influenzae LKP16 (88-0715);

H. influenzae LKP18 (88-0909);

H. influenzae LKP19 (88-1219); and

H. influenzae LKP20 (88-1225).

In one embodiment of this method, there is provided a method wherein the vaccine composition comprises pili agglutinable by antisera derived from pili from organisms of at least LKP 10. In another embodiment, there is provided a method wherein the vaccine composition comprises pili agglutinable by antisera derived from pili derived from organisms of each of the strains of H. influenzae LKP9 through LKP16 and LKP18 through LKP20. Yet another embodiment comprises a method wherein the vaccine composition comprises pili derived from organisms of each of the strains of H. influenzae LKP9 through LKP16 and LKP18 through LKP20.

The fourth embodiment comprises a mammalian antiserum specific against one of the H. influenzae pilus LKP types. Such an antiserum is made applying steps known to those skilled in the art to the purified pili described above.

DESCRIPTION OF DRAWINGS

FIG. 6. Table 2: Cross-reaction table for LKP Pili and antisera thereto.

DETAILED DESCRIPTION OF THE PREFERRED EMBODIMENTS

Figure 1:
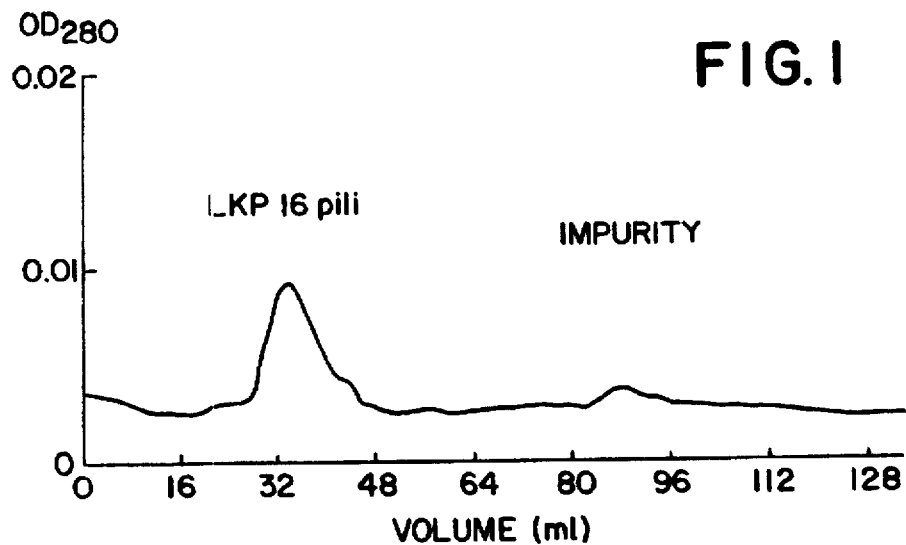
FIG. 1. Purification of intact LKP16 (88-0715) pili on a molecular sieve column.
Figure 2A:
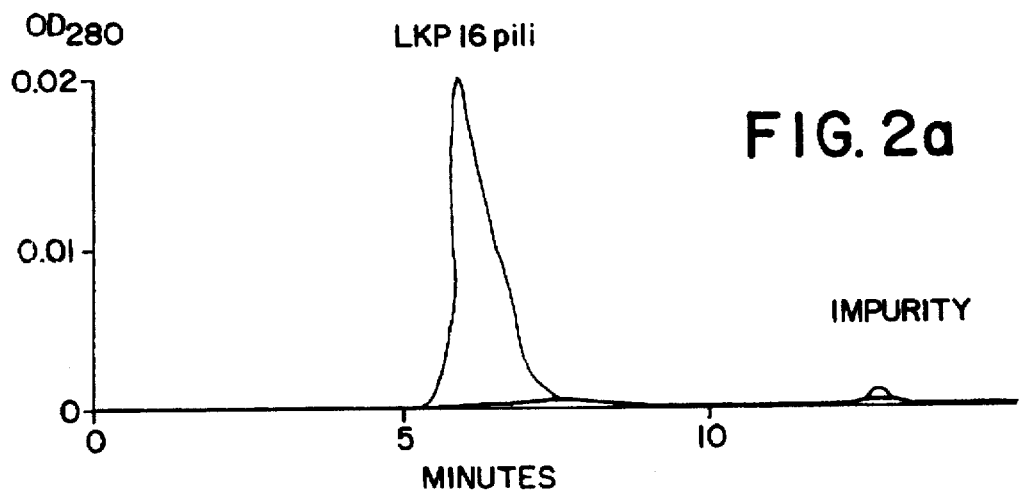
FIG. 2. Purification of intact LKP16 (88-0715) and LKP19 (88-1219) pili on an HPLC column.
Figure 2B:
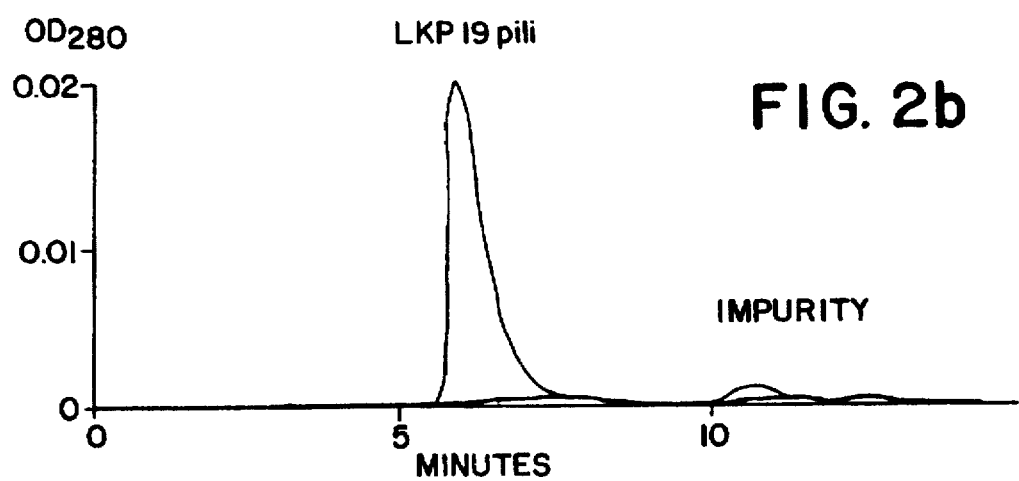
Figure 3:
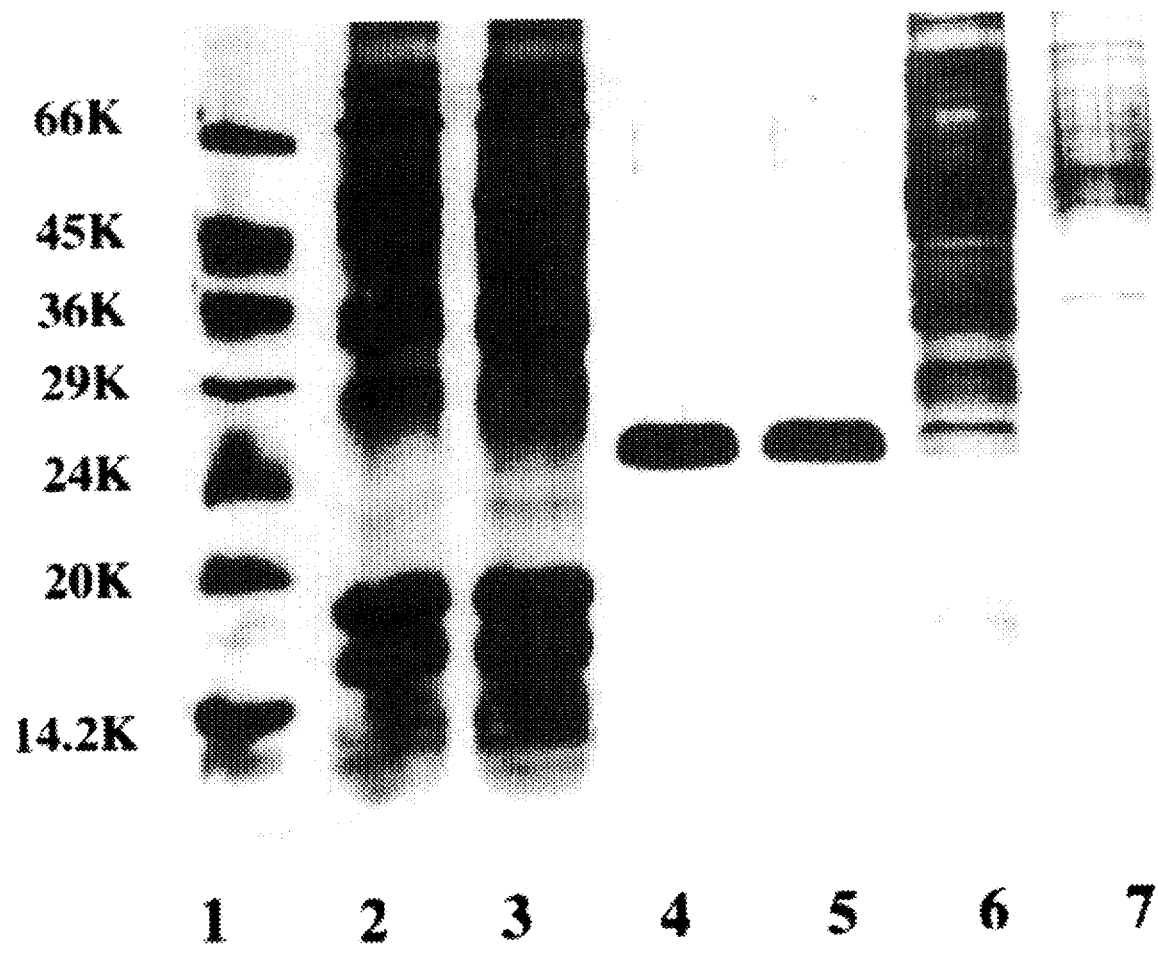
FIG. 3. SDS Gel electrophoresis of intact LKP11 pili
Figure 4:
FIG. 4. Electron micrograph of recombinant E. coli expressing LKP11 pili.

A. Making and Purifying the H. influenzae pili

The first step in producing the purified pili is the phase selection and piliated phase cloning of a pilus producing strain. An H. influenzae throat isolate is subjected to phase selection by hemadsorption and by phase cloning (employing colony picking and restreaking). Hemagglutination is performed at standard bacterial concentrations for standard times at room temperatures using human red blood cells in PBS. The colonies of the resulting culture are all or nearly all HA+.

If one is purifying a known serotype, one also tests for serum agglutination so that all or nearly all colonies agglutinate in one and only one of the known typing sera. The exception is when one is trying to simultaneously purify more than one pilus type from a multiple type producing strain. In order to avoid multiple expression of LKP serotypes, and the resulting mixture of LKP pili types, one manipulates and maintains the phase composition of the production culture throughout the production cycle. Both the inoculum and the harvest are monitored for phase composition by spread plating and testing individual colonies Growth and harvesting of the production culture. A solid phase fermentation method is used for H. influenzae, in which large trays of agar medium are inoculated by spreading with glass rod spreaders and harvested by scraping with glass plates. E. coli may also be grown under the solid phase method, although a liquid phase fermentation is preferred due to the bacterium's more rapid growth thereunder. The inoculum size should be relatively large to keep incubation times and piliation phase losses to a minimum. The best growth conditions for pilus production per bacterial cell are not necessarily the same as those for best piliated phase stability. The conditions of choice for H. influenzae pilus production are on chocolate agar at 37° C. in 80% humidity and air containing 5% $CO_2$. Trays are usually incubated for 15 hrs to 24 hrs before harvesting. Harvesting buffer is usually used to aid in removing the maximum amount of growth from the trays. A minimum amount of harvesting buffer is recommended in order to maintain bacterial density as high as possible. High density bacterial cultures aid in the mechanical removal of pili by blending and in the precipitation of free pili from the culture fluid.

The harvested bacteria are monitored for phase composition by spread plating and colony testing for hemagglutination and serum agglutination. The solid phase method has the advantages over the liquid phase method of giving high bacterial concentrations without an additional centrifugation step and of avoiding the production of aerosols.

Removal of Pili. Next, the pili are removed from the bacteria by viscous shearing. Shearing forces are increased when the blender speed is higher, the blender cup is smaller, the pitch of the blender blades is higher and the edges of the blender blades are sharper. Efficient removal conditions are determined empirically and monitored by electron microscopy. The most accurate way is to measure pilus removal at different blender speeds and configurations (a blending spectrum) and use those conditions that just remove most of the pili. If excessive heat is generated during the process the blender cup must be cooled.

An alternative method of removing attached pili is by heat. Heating at from 40° C. to 70° C. for from 5 to 30 min can efficiently remove shorter and thinner pili from H. influenzae under conditions where standard blending conditions cannot. The danger in this procedure is that pilus proteins may be denatured and/or minor pilus proteins could be damaged or removed. It is generally better to remove shorter or thinner pili by increasing the shearing forces of the mechanical removal procedure.

Isolation of Pili. In the next step, one removes pili from the suspension while leaving the contaminating proteins and other contaminants in the centrifugation supernatant fluid. The pili are longitudinally aggregated ("crystallized") so that low speed centrifugation or filtration can specifically remove them. Aggregated pilus crystals or clumps can be many times larger than bacterial cells.

Pilus rods in suspension can be cycled between a free single rod state and an aggregated ("crystalline") state by adjusting solvent conditions. Thus, the buffering conditions for bacterial removal are adjusted to higher pH values (typically pH8 to pH10) with an appropriate buffer of adequate buffering capacity. The molarity of the buffer is also lowered to increase intact pilus solubility. Bacterial cells are then removed at clarifying centrifugation speeds. The adjustment of harvesting conditions is done by the addition of a harvesting buffer. One must use buffers of sufficient ionic strength so that buffering capacity is maintained. Otherwise, the buffering capacity of the bacterial products and residual bacterial metabolism will alter the pH away from the optimal range.

Five of the most effective solvent conditions for the manipulation of pilus solubility are pH, salt concentration, ionic species, aqueous polymers and detergents. Often, more than one of these conditions is used in a series of cycling steps. Pilus crystals are separated from soluble contaminants by centrifugation of the crystals into a pellet. Free single pili are separated from particulate contaminants by centrifuging the particulates into a pellet. The alternate pilus crystallization and crystal removal to a pellet followed by pilus solubilization and impurity removal to a pellet is termed "cycling".

pH adjustment may be used to purify Hflu LKP pili. The principle is to titrate the ionizable groups on the lateral surface of the pilus rod until the charge density and charge pattern are such as to permit longitudinal association. For best purity and yield, it is desirable to allow pilus crystals to form slowly and completely, this can be accomplished by using overnight dialysis to achieve pH changes.

Aqueous polymers, such as polyethylene glycol (PEG) and dextran are very useful in pilus purification since they preferentially aggregate highly asymmetric (rod shaped) protein molecules. PEG is often used in LKP pilus purification, especially in the first cycling step after removal of depiliated bacteria when the largest concentrations of impurities are present. For resolubilization of pilus rods, the pellet of crystals is resuspended in PEG-free buffer.

Besides detergent extraction and PEG precipitation, LKP pili also can be purified by HPLC, FPLC and other column methods. These methods are particularly good when working with unknown LKP pili believed to present a new serotype. Normally, pili are partially purified by extraction and precipitation first until the pilus solution is clear, concentrated and very small size. If SDS-PAGE does not purify the preparation, column methods are applied. Sizing columns are preferred to be used for this purpose. Prior to column loading, it is important that the detergent used for partial purification of the pili be removed. The presence of a detergent significantly reduces the column's separation resolution. This removal may be performed by dialysis or other suitable methods. Size exclusive columns require a small sample volume. For HPLC or FPLC, the loading volume of 50 μl to 200 μl is recommended and for other routine LC gel filtration columns, the sample loading volume depends on the length and size of the column. A 1 ml pilus sample is preferred for a column with a total volume of 50 ml. Since pili have a low absorbance at 280 nm, a high sensitivity monitor is recommended. If it is available, protein eluted from column can be monitored at 230 nm.

Further methods suitable for isolating the pili from other cell constituents employ density gradient methods which are well known to those skilled in the art.

The preferred procedure of isolating pili involves their mechanical removal from harvested bacteria and their separation from the bacterial cells by centrifugation. Pili are concentrated and further purified by alternate cycles of longitudinal aggregation (crystallization) of intact pilus rods with soluble impurities removed by centrifugation of the crystals followed by solubilization of the pilus crystals into free pilus rods with particulate impurities removed by centrifugation.

B. Making and Purifying LKP pili from transformed *E. coli*

It is reasonable to expect that the pilin, chaperone, anchor, minor tip and large minor tip adhesin proteins of an *H. influenzae* pilus must interact with each other during the pilus assembly process. Accordingly, it is believed that the best approach to the synthesis of pili in a recombinant organism is to clone the whole operon of each type of LKP pilus desired into *E. coli*. Three different *E.coli* recombinant strains each produce good quantities of a single type of LKP pilus, LKP10, LKP11, and LKP12, which are easily purifiable. The piliation of these strains is stable. They can be grown as *E. coli* in liquid phase as needed for large scale industrial fermentation of vaccine antigens. The single pilus types they produce can be purified and standardized individually, before mixing in the desired proportions with other pilus types to form a multivalent vaccine.

The general methods for the genetic construction of these strains are the same as those used for the cloning of the LKP1 operon, described in U.S. patent application Ser. No. 08/277,231. Some of these methods are typical for the genetic cloning of any genes into *E. coli* and some of them are particular to the successful cloning of *H. influenzae* LKP pilus operons into *E. coli*. The generally applicable methods will be described first. For whole operon cloning, an *H. influenzae* DNA library is constructed using a suitable plasmid as a genetic vector. Suitable plasmids are, generally, purchased from manufacturers of kits containing the plasmids, enzymes and instructions needed for cloning. The source of LKP pilus operon DNA is genomic DNA extracted from an Hflu strain selected from our collection and expressing the LKP pilus type to be cloned. Vector plasmid DNA is extracted from bacteria containing the vector. *H. influenzae* DNA is partially cleaved with the appropriately specific restriction endonuclease enzyme(s) to create DNA fragments of suitable size and with suitably specific "sticky ends" for ligating to the vector DNA. The size distributions are monitored by gel electrophoresis. The vector DNA was also cleaved by suitably specific endonucleases to create "sticky" ends that would permit association with and ligation to the ends of the *H. influenzae* DNA fragments.

These DNA fragments are mixed with the *E. coli* vector DNA fragments in the presence of ligating enzymes and other necessary factors which covalently joined the *H. influenzae* fragments to the vector fragments. This "library" of vector plasmids (or phages) containing *H. influenzae* DNA was used to transform (plasmids) or transfect (phages) into a suitable *E. coli* host for the vector. For certain vectors used to carry large DNA fragments (cosmids), the vector DNA was "packaged" in vitro into phage particles for efficient transfection. The vectors were also designed to contain suitable antibiotic resistance markers to allow for the selective growth of only those *E. coli* host cells that receive an intact replicating vector. Thus, the transformed or transfected cultures are plated on antibiotic-containing agar to allow for the growth of colonies (clones) each containing a vector with a single kind of *H. influenzae* DNA fragment. A few of the colonies, those containing an intact LKP pilus operon, in a vector able to replicate well in the host strain, in a host strain able to transcribe and translate the LKP operon genes, and able to assemble and excrete intact LKP pili, contain bacteria which would express pili on their surfaces.

These few colonies could be recognized among the other nonpiliated ones on the Petri dish by a pilus antiserum colony blot method. A piece of nitrocellulose paper is pressed gently onto the colonies on the dish in order to remove a bacterial sample of each colony to the paper in the same pattern the colonies were present on the Petri dish. The piece of paper containing the colonial material blotted on it is then incubated with a suspension of type-specific LKP pilus antibodies raised in lab animals (rabbits). If the bacteria express LKP pili of that specific type, they bind to the pili and cover the bacteria. The paper is then incubated with a second antibody conjugated to an enzyme capable of catalyzing a color-producing reaction in situ on the colonies of piliated bacteria. Colonies on the Petri dish in positions where LKP pilus antibodies label the sampled bacterial material are presumed to be composed of bacteria expressing H. influenzae LKP pili of the desired type and are then picked and restreaked (cloned) for further analysis.

E. coli strains identified as producing LKP pili may be cultured in a liquid phase or a solid phase fermentation method; the former however is generally preferred since E. coli cell cultures grow much more quickly therein. In the liquid phase method, growth medium in glass flasks or stainless steel fermentation vessels in inoculated. The medium of choice depends on the particular LKP pilus. The incubation temperature is 37° C. and the culture is gassed with air while being mechanically agitated. Liquid phase fermentation of vaccine strains can be scaled up for growth in industrial fermentors as needed for commercial vaccine production. The bacterial culture is concentrated by centrifugation (or filtration) after it is prepared by the addition of harvesting buffer for the efficient removal of free pili frofluid culture fluid and attached pili from the bacteria.

The genetic code enables one to identify the amino acid sequence of an LKP pilin molecule from the DNA encoding the pilin. Thus, from the three DNA sequences encoding the LKP1, LKP10 and LKP11 pili, one may deduce the first twenty-five amino acid residues at the N-terminal are, respectively:

LKP1 H₂N-ADPQV STETS GKVTF FGKGG ENTCK VKTDS KNMSV

LKP10 H₂N-ATTHT STVGG TTAGK AXDGS TPGTN SG...

LKP11 H₂N-ATNQV TGSNI GTTTP GKATD GSAPG ENSGV VRSTS

It is seen that there is a significant amount of homology even between these fragments of the pilin proteins of the different LKP serotype pili.

C. Characterizing Purified Pili

Criteria of purity and homogeneity for LKP pili: The usual six criteria for judging the purity and homogeneity are applied to the LKP pili. First, the ostensibly purified pili are subjected to polyacrylamide gel electrophoresis on an SDS gel. The gel is stained with either silver, or with coomassie blue. There should be observed two bands, one strong band indicating pilin, and a faint band representing adhesin. Second, one examines the pili samples with an electron microscope to ascertain whether pili are present. Third, one examines the pili samples with a dark field light microscope to determine whether the longitudinal aggregates typical of pili (pseudo-crystals) are present. Next, the pilus sample is subjected to UV spectroscopy; the absorption spectrum indicates the presence of protein and absence of nucleic acids. It should be noted that the silver stain of the polyacrylamide gel also reveals the presence of lipopolysaccharides. Fifth, the pilus sample is exposed to a series of antisera to several different LKP serotypes to see which react with the pilus. If there is no cross-reaction with known antisera, and an antiserum to the new phli does not cross react with other recognized LKP types, one can be relatively certain that one has isolated a new single type of LKP pilus. Finally, the purity of the pilus sample should be assessed using HPLC or gel filtration; a single peak from either indicates that the pili in the sample are homogeneous. The purity and homogeneity of the pili can be confirmed by testing the column peak against the known LKP antisera.

The gel electrophoresis, electron microscopy, dark field microscopy, ultraviolet spectroscopy and serotype cross reaction methods employed in examining the purity and homogeneity of the LKP pili are those known to persons skilled in the art.

Using high resolution transmission electron microscopy, and different contrast enhancement and particle spreading methods (adhesion negative stain, agar filtration negative stain, metal shadowed negative stain, metal shadowed protein monolayer spreading, immunogold labeled metal shadowed and immunogold labeled negative stain), the isolates from the bacterial epidemiology study were examined for pilus morphology and distribution. The following scoring system was used for each parameter. Diameters were scored only as 3 (3 nm) or 4 (4 nm) since these were the only two diameters observed. The 3 nm pili were formerly called thin and the 4 nm pili thick. The lengths of pili were averages and were scored as 0 (no pili), 1 (average length <0.2 microns), 2 (average length 0.2 to 0.5 microns) and 3 (average length >0.5 microns). Quantitative pilus expression, which reflected both pilus number per cell and fraction of piliated cells, was scored as 0 (no pili), 1 (poor piliation), 2 (fair piliation) and 3 (good piliation).

D. Anti-LKP Pilus Antisera

It is entirely unnecessary to include all kinds of pilus antigens, much less any other H. influenzae antigens expressed by the causative bacterial pathogen in a PSF1 pilus vaccine for it to be totally effective. This includes other kinds of pili, capsules, flagella, outer membrane proteins or lipopolysaccharide components. The tetravalent E. coli pilus vaccine developed by Applicant is essentially 100% effective in challenge experiments and in the field and at several U.S. locations, even though the E. coli isolated from piglets may express at least 9 families or types of pili that are not contained in the vaccine. One can infer from this that an H. influenzae LKP pilus vaccine is likely to protect effectively against otitis media even though other classes of pili and other antigens are expressed by H. influenzae.

Matured young New Zealand rabbits are immunized subcutaneously with 200 µg purified pilus protein mixed with Freund's incomplete adjuvant. 3 injections are given at 4-week intervals. After the last booster injection, the animals are bled through the marginal ear vein and serum prepared by standard methods. The serum is titrated for anti-pilus antibodies using piliated bacteria agglutination using techniques well known to those skilled in the art.

The frequency of each LKP serotype in the bacterial epidemiological study is determined for all H. influenzae cultures expressing typical LKP pili. The serotype frequency is determined by counting LKP serotypes on both single expressors and multiple expressors. Fifteen of the nineten serotypes are found on typically LKP piliated cultures, and 90% of these cultures were serotypable in the 19-type system. The frequency distribution of serotypes for these cultures is shown in Table 1.

It is significant for vaccine design that some serotypes occurred more frequently than others. For typically LKP piliated isolates, at least one of the 9 most frequently occurring LKP serotypes was found on 76% of the isolates. From this, one could conclude that a multivalent intact LKP pilus vaccine containing a modest and practicable number of LKP pili serotypes would confer significant protection against otitis media if field-tested.

TABLE 1

Distribution of LKP serotypes, and pilus morphology traits, among antiserum-agglutinable strains examined by EM

|  |  | L = 1 | L = 2 | L = 3 | D = 3 | D = 4 | % of total |
|---|---|---|---|---|---|---|---|
| LKP9 | N = 0 | 0 | 0 | 0 | 0 | 0 | <1 |
| LKP10 | N = 26 | 1 | 8 | 17 | 2 | 24 | 23 |
| LKP11 | N = 22 | 0 | 6 | 16 | 0 | 22 | 19 |
| LKP12 | N = 12 | 0 | 3 | 7 | 2 | 8 | 10.5 |
| LKP13 | N = 0 | 0 | 0 | 0 | 0 | 0 | <1 |
| LKP14 | N = 9 | 1 | 2 | 6 | 1 | 8 | 8 |
| LKP15 | N = 6 | 0 | 5 | 1 | 0 | 6 | 5 |
| LKP16 | N = 9 | 0 | 4 | 5 | 3 | 6 | 8 |
| LKP18 | N = 12 | 1 | 4 | 7 | 1 | 11 | 10.5 |
| LKP19 | N = 3 | 0 | 1 | 2 | 0 | 3 | 2 |
| LKP20 | N = 15 | 1 | 6 | 8 | 3 | 12 | 13 |
| Total Strains | = 114 | 4 | 39 | 69 | 12 | 100 |  |

N = number of strains exhibiting that LKP serotype
L = 1 indicates length of < 0.2μ
L = 2 indicates length of > 0.2μ and < 0.5μ
L = 3 indicates length of > 0.5μ
D = 3: pilus diameter = 3 nm ("thin")
D = 4: pilus diameter = 4 nm ("thick")

It is expected that the worldwide LKP pilus serotype pattern will be similar to the greater Pittsburgh pattern, in view of: the limited number of pilus serotypes in *E. coli*; and the similarity of the ecological niche (i.e., the human nose and throat) throughout the world.

Testing of the new LKP serotypes against those already established, and against each other, results in characteristic cross-reaction patterns for each LKP serotype. These are presented in Table 2 in FIG. 6, a cross-reaction table among all the LKLP serotypes.

E. Formulating Vaccine Compositions against *H. influenzae*. The purified LKP pili may be administered via an infectious construct, such as a replication incompetent or attenuated viral construct; a recombinant host cell (such as, a mammalian cell) which will express the protein in vivo; or as a vaccine composition. Vaccine compositions may incorporate one or more LKP pilus types from *H. influenzae*, transformed *E. coli*, or both. The infectious construct, recombinant host cell and vaccine composition may be made by methods known to person skilled in the art.

The vaccine composition may be administered orally, e.g., in capsule form, or by subcutaneous, intradermal, or intramuscular injection. Where the mode of administration is injection, any pharmaceutically acceptable suspending medium may be employed. It has been found especially useful to employ phosphate buffer, suitably containing merthiolate, as the vehicle or suspending medium. It is preferred to use 0.0005–0.1, most suitably 0.0004M phosphate buffer, at ionic strength containing 0.0005 to 0.1%, and, suitably 0.01% merthiolate. The vaccine composition may optionally include an adjuvant. Suitable adjuvants include adjuvant materials known to those skilled in the art.

The concentration of pili in the vehicle is not critical. The main criterion of desirability is that the pili shall be sufficiently finely divided to provide a suspension which meets generally accepted standards of syringeability. Since there are no local or systemic toxic effects engendered by the injection of vaccine, there appear to be no upper limits to the dosage administered. It has been found suitable, however, to administer between 1 and 100 micrograms of pili per kilogram of body weight, most suitably about 20 micrograms per kilogram of body weight, per injection. The foregoing amounts refer to total pilus protection. Thus, if all eleven of the new LKP pilus serotypes are to be employed in the vaccine composition, the total amount of pili would still be approximately 20 mg per kg of body weight per injection.

It is generally preferred to administer the vaccine composition in more than one dose separated by a predetermined time interval. This time interval is selected to permit the formation of an adequate titer of antibodies to the pili in the injected subject.

The following is a description of the general growth and purification procedures that were found to give acceptable yield and purity of LKP pili. Exceptions to the general procedure are noted. The stock and medium formulae set forth in Formulae I through XIV are incorporated herein by reference from U.S. Pat. No. 5,336,490 as if set forth herein.

EXAMPLE I

An *H. influenzae* strain isolated from the throat of a child may be grown overnight on Brain Heart Infusion Agar (DIFCO) supplemented with 10 μg each of AND (Sigma, N7004) and Hemin (Sigma H2250) (S-HBIA—Formula II) at 37° C. with 80% relative humidity and 5% $CO_2$. If the original isolate contains no piliated bacteria detectable by hemagglutination or electron microscopy, the culture may be enriched for piliated phase bacteria by hemabsorption following the procedures described in "A Hemabsorption Method for Detection of Colonies of *Haemophilus influenzae* Type b Expressing Fimbriae," Connor, E. M. and M. R. Loeb, *Journal of Infectious Diseases*, Vol. 148, pp. 855–860 (1983), incorporated herein by reference. Aliquots of piliated ($P^+$) and non-piliated ($P^-$) strains may be isolated and stored at $-70°$ C. using 5.5% Dimethyl Sulfoxide (DMSO) in Tryptic Soy Broth (TSB) as cryoprotectant.

EXAMPLE II

General Outline of purification of *H. influenzae* pili
Part A: Inoculum Preparation, Growth and Harvest Frozen piliated ("$P^+$") cultures of *H. influenzae* (86-0807), expressing LKP10 serotype pili, are thawed and plated on supplemented brain-heart infusion agar. Plating is performed 18–20 hours before the anticipated tray inoculation. The plates are incubated at 37° C., with 80% relative humidity and 5% $CO_2$. The percentage of the colonies having hemagglutinating activity is assessed. Generally, ten individual colonies are picked and assayed. In all cases, at least nine out of 10 colonies are $HA^+$ for human red cells.

Trays of GC base supplemented with DSF and hemin were inoculated with hemagglutinating bacteria isolated as described above. These bacteria are suspended in a culture transfer solution. The transfer solution is a potassium phosphate buffered saline solution containing 5 mg/ml beta-NAD. Bacteria are scraped from the plates with dacron swabs and suspended in the transfer solution until visibly turbid. Each tray is then inoculated with 2.5 ml A glass spreader is used to distribute the inoculum evenly over the surface of the medium. Inoculated trays are incubated for 20 hours at 37° C. with 5% $CO_2$ and 80% relative humidity.

Growth is scraped from the agar using a metal scraper and 5–10 ml of harvest buffer per tray. Since the cells are being washed before blending, the harvest buffer is at pH 5 to crystallize and recover any pili which had been shed.

Part B: Blending and Initial Stages of Cycling

Each cell pellet from Part A is resuspended in a volume of blending buffer such that the suspension volume is 150–200 ml, or about 5 ml of buffer per gram of wet cell pellet. The pellet is not completely resuspended but instead broken up sufficiently so that it could be removed from the centrifuge bottle. Blending is performed using the large cup and unmodified blade assembly of the Omni mixer. Each resuspended pellet is blended for 3 minutes at a speed of 10–11 k rpm. After blending, "depiliated" cells are removed by centrifugation at 15,300×g, for 20 minutes. The supernatant is poured off and further clarified by another centrifugation at 15,300×g, for 20 minutes. The supernatant is poured off and the cell pellets discarded.

The first crystallization is performed by dialysis of the crude supernatant against a pH 5 acetate buffer. Dialysis is performed against 20 volumes of buffer overnight at 4° C. Crystalline pili, appearing as large chunky aggregates in the darkfield, are sedimented for 60 minutes at 4° C. and 22,100×g. The supernatant is poured off and discarded. The pellets are inverted over paper towels to drain briefly. This point marks the end of the first cycle.

Solubilization of the pellets is performed by resuspension in 0.01M CAPS buffer, at half the original crude volume. The pellets are broken up by the use of a rubber policeman and by drawing the pellets into and out of a 10 ml pipette. The pellets, brown in color, are then allowed to solubilize at 4° C. with no stirring for several hours or overnight. The preparation is clarified by centrifugation at 22,100×g for 60 minutes. The preparation is loaded into dialysis tubing then dialyzed against 50 mM sodium acetate buffer pH 5. Dialysis is performed in the cold overnight. Pilus aggregates are then collected and centrifugation of dialysis to the content. This point marks the end of the second cycle.

The third cycle is identical to the second, except that the volume of solubilizing buffer used is half of that used in the second cycle.

Part C: Final Stages of Cycling

After 3 cycles, the preparation still carries a faint yellow color, although it seems fairly clean by SDS-PAGE. The following cycles are performed to remove additional impurities.

Crystalline pili are sedimented by centrifugation at 22,100×g. Pili are solubilized in a pH 10.5 phosphate buffer containing 5 m. M EDTA and 0.2% Triton X-100 (PBET). The same volume as in the previous cycle is used. Solubilization is performed at 4° C. with occasional mild stirring and is usually completed within 4 hours. Clarification is performed by centrifugation at 22,100×g for 60 minutes. The supernatant is carefully poured off, leaving a clear gelatinous pellet.

Sodium chloride and polyethylene glycol are used as the crystallizing agent in the 4th cycle. However, to facilitate crystallization, it is necessary to first lower the pH from 10.5 to 7.5–8.0 by titration with HCl. The pili, still soluble at this stage, are crystallized by adding 5M sodium chloride to a final concentration of 0.5M and 30% PEG to a 3% final concentration. Streaming birefringence is visible immediately. The preparation is held at 4° C. for 1 hour and then the "crystalline" pili sedimented by centrifugation at 22,100×g for 60 minutes. This point marks the end of the 4th cycle.

The yellow supernatant is poured off and discarded and the pellets inverted to drain. Solubilization is performed again in the PBET, followed by clarification by centrifugation at 22,100×g for 60 minutes. Again, after removal of the supernatant, a clear gelatinous pellet remains. This point marks the end of the 5th cycle.

The 6th cycle is identical to the 5th, except that the pH 10.5 phosphate buffer used for solubilization does not contain EDTA or Triton X-100.

The preparation is stored soluble, in the final pH 10.5 phosphate buffer, with 0.02% sodium azide as a preservative.

EXAMPLE III

Genomic DNA is selected to make *E. coli* recombinants from *H. influenzae* CB59 (LKP11), *H. influenzae* 88-0807 (LKP10) and *H. influenzae* 88-0677 (LKP12). Hemagglutination and serum agglutination are examined before making the genomic library to confirm the presence of the desired LKP pilus type. *E. coli* strains XL1-Blue$^{MR}$ and HB101 were used as a cloning host cell.

DNA library construction and cosmid vector DNA: Genomic DNA from the LKP11, LKP10 and LKP12 strains is extracted and purified by standard methods well known to those skilled in the art. The genomic DNA isolated from each strain, approximately $1.8 \times 10^6$ bp, is partially digested with restriction enzyme Sau3A I. The three genomic DNA fragments, of approximately 30 kb size, are run separately on an LMTA-gel (Sigma) and are then purified by the phenol-chloroform method. The final DNA concentration is about 1 µg/ul.

Vector DNA SuperCos I (Stratagene, La Jolla, Calif.) is digested with Xba I and dephosphorylated with calf intestinal alkaline phosphatase (CIAP). The Xba I and CIAP treated vector DNA is then digested with Bam HI restriction enzyme. A vector fragment of approximately 6.5 kb is obtained.

A DNA fragment from *H. influenzae* CB59 is ligated at the Bam HI site of the vector DNA SuperCos I. The ligated DNA is packaged into separate 1 phage particles using Cigao-pack Gold kit (Stratagene, La Jolla, Calif.). The host cell for packaging was XL1-Blue$^{MR}$. This is repeated separately for each of the DNA fragments from 88-0807 and 88-0677 respectively.

Library screening: Recombinants expressing LKP type pili are screened by colony blot method. The concentration of anti-pilus antisera for LKP11, LKP10 and LKP12 is 1:1000 dilution. The percentage of positive colonies is 40/4200 for LKP11, 9/700 for LKP10 and 1/600 for LKP12, and is confirmed by EM. The recombinants are verified by further HA and SA assay and are named CLJ11 for LKP11, CLJ10 for LKP10 and CLJ12 for LKP12.

Figure 5:
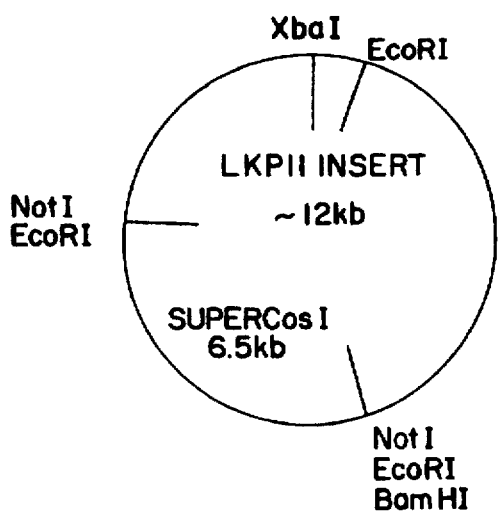
FIG. 5. Restriction maps for vectors carrying the operon for LKP10, LKP11 or LKP12 pilus of H. influenzae incorporated into the SuperCosl vector.
Figure 5:
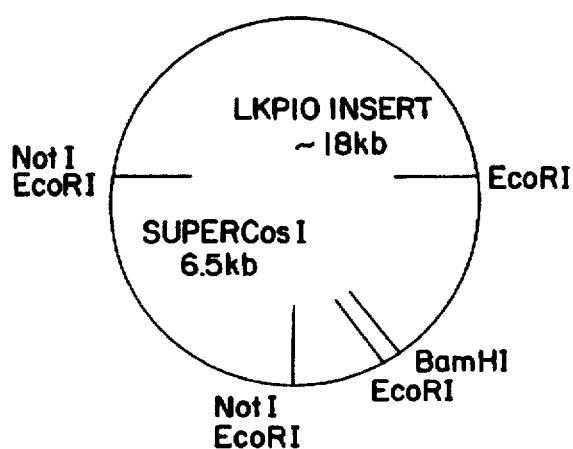
Figure 5:
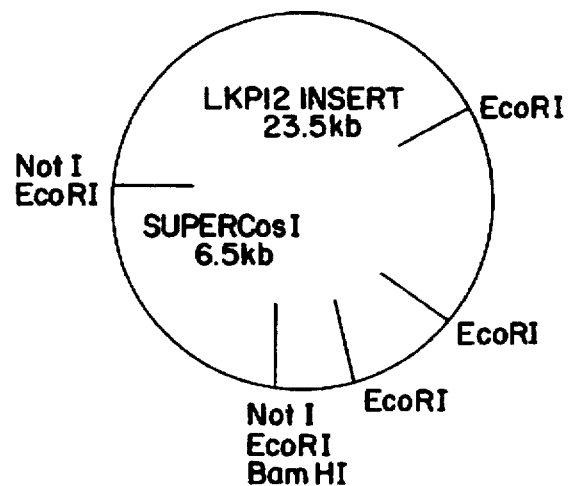

The DNA of the recombinants is extracted and used to transform *E. coli* strain HB101 because XL1-Blue cell expresses type I pili. The CUl1 DNA size of approximately 18.5 kb is obtained by digestion and subsequent ligation using restriction site on insert and vector DNA. CLJ10 DNA is approximately 25 kb and CLJ12, 35 kb. The restriction maps of the three vectors in FIG. 5 are obtained by restriction enzyme digestion.

I claim:

1. Purified whole *H. influenzae* LKP pili having serotypes selected from the group consisting of LKP9 through LKP 16 and LKP18 through LKP20, previously separated from other *H. influenzae* components, said pili being aaglutinable by at least one antiserum selected from the group consisting of antisera derived from purified LKP pili, previously separated from other *H. influenzae* components, derived from one of the following organisms:

*H. influenzae* LKP9 (86-0214) ATTC 55771;

*H. influenzae* LKP10 (86-0807) ATTC 55772;

*H. influenzae* LKP11 (CB-59) ATTC 55773;

*H. influenzae* LKP12 (88-0677) ATTC 55774;

*H. influenzae* LKP13 (86-0762) ATTC 55775;

*H. influenzae* LKP14 (88-0473) ATTC 55776;

*H. influenzae* LKP15 (89-1163) ATTC 55777;

*H. influenzae* LKP16 (88-0715) ATTC 55778;

*H. influenzae* LKP18 (88-0909) ATTC 55779;

*H. influenzae* LKP19 (88-1219) ATTC 55780; and

*H. influenzae* LKP20 (88-1225) ATTC 55781.

2. The purified whole *H. influenzae* LKP pili of claim 1 derived from the group of *H. influenzae* strains consisting of:

*H. influenzae* LKP9 (86-0214) ATTC 55771;

*H. influenzae* LKP10 (86-0807) ATTC 55772;

*H. influenzae* LKP11 (CB-59) ATTC 55773;

*H. influenzae* LKP12 (88-0677) ATTC 55774;

*H. influenzae* LKP13 (86-0762) ATTC 55775;

*H. influenzae* LKP14 (88-0473) ATTC 55776;

*H. influenzae* LKP15 (89-1163) ATTC 55777;

*H. influenzae* LKP16 (88-0715) ATTC 55778;

*H. influenzae* LKP18 (88-0909) ATTC 55779;

*H. influenzae* LKP19 (88-1219) ATTC 55780; and

*H. influenzae* LKP20 (88-1225) ATTC 55781.

3. A multivalent intact pilus vaccine composition for protecting subjects against infections caused by piliated *Haemophilus influenzae* organisms which comprises a pharmaceutically acceptable carrier and at least one of the purified whole *H. influenzae* LKP pili of claim 1.

4. The vaccine of claim 3 wherein said purified whole *H. influenzae* LKP pili are agglutinable by at least one antiserum selected from the group consisting of antisera derived from purified LKP pili derived from *H. influenzae* LKP10 (86-0807) and *H. influenzae* LKP11 (CB-59).

5. The vaccine of claim 3 comprising purified whole *H. influenzae* LKP pili of each of serotype LKP9 through LKP16 and LKP18 through LKP20.

6. The vaccine of claim 3 comprising purified whole *H. influenzae* LKP pili derived from each of the *H. influenzae* of claim 3.

7. A method of immunizing subjects against infections caused by piliated *H. influenzae* organisms which comprises administering to a subject in need of protection a vaccine composition which raises the antibody level of the subject to a level sufficient to provide such protection comprising:

whole *H. influenzae* LKP pili of at least one type selected from the group of serotypes of claim 1.

8. The method of claim 7 wherein the vaccine composition comprises pili agglutinable by at least one antiserum selected from the group consisting of antisera derived from purified LKP pili derived from *H. influenzae* LKP10 (86-0807) and *H. influenzae* LKP11 (CB-59).

9. The method of claim 7 wherein the vaccine composition comprises purified whole *H. influenzae* LKP pili of serotype LKP9 through LKP16 and LKP18 through LKP20.

10. A method of claim 7 wherein the vaccine composition comprises purified whole *H. influenzae* LKP pili previously separated from other *H. influenzae* components, derived from each of the following organisms:

*H. influenzae* LKP9 (86-0214) ATTC 55771;

*H. influenzae* LKP10 (86-0807) ATTC 55772;

*H. influenzae* LKP11 (CB-59) ATTC 55773;

*H. influenzae* LKP12 (88-0677) ATTC 55774;

*H. influenzae* LKP13 (86-0762) ATTC 55776;

*H. influenzae* LKP14 (88-0473) ATTC 55776;

*H. influenzae* LKP15 (89-1163) ATTC 55777;

*H. influenzae* LKP16 (88-0715) ATTC 55778;

*H. influenzae* LKP18 (88-0909) ATTC 55779;

*H. influenzae* LKP19 (88-1219) ATTC 55780; and

*H. influenzae* LKP20 (88-1225) ATTC 55781.

* * * * *